(12) United States Patent
Andina et al.

(10) Patent No.: US 10,881,737 B2
(45) Date of Patent: Jan. 5, 2021

(54) TWO-COMPONENT SYSTEM

(71) Applicant: STRAUMANN HOLDING AG, Basel (CH)

(72) Inventors: Diana Andina, Zurich (CH); Aaldert Molenberg, Binningen (CH); Heiner Bieli, Basel (CH)

(73) Assignee: STRAUMANN HOLDING AG, Basel (CH)

( * ) Notice: Subject to any disclaimer, the term of this patent is extended or adjusted under 35 U.S.C. 154(b) by 215 days.

(21) Appl. No.: 15/737,472

(22) PCT Filed: Jun. 16, 2016

(86) PCT No.: PCT/EP2016/063839
§ 371 (c)(1),
(2) Date: Dec. 18, 2017

(87) PCT Pub. No.: WO2016/202907
PCT Pub. Date: Dec. 22, 2016

(65) Prior Publication Data
US 2018/0185493 A1 Jul. 5, 2018

(30) Foreign Application Priority Data
Jun. 16, 2015 (EP) .................................... 15172329

(51) Int. Cl.
| A61K 47/32 | (2006.01) |
|---|---|
| A61K 8/43 | (2006.01) |
| A61Q 11/00 | (2006.01) |
| A61K 9/00 | (2006.01) |
| A61K 31/155 | (2006.01) |
| A61C 5/64 | (2017.01) |
| A61P 1/02 | (2006.01) |
| A61K 8/04 | (2006.01) |
| A61K 8/20 | (2006.01) |
| A61K 8/81 | (2006.01) |
| A61K 9/06 | (2006.01) |
| A61K 33/20 | (2006.01) |

(52) U.S. Cl.
CPC ................ *A61K 47/32* (2013.01); *A61C 5/64* (2017.02); *A61K 8/042* (2013.01); *A61K 8/20* (2013.01); *A61K 8/43* (2013.01); *A61K 8/8147* (2013.01); *A61K 9/0063* (2013.01); *A61K 9/06* (2013.01); *A61K 31/155* (2013.01); *A61K 33/20* (2013.01); *A61P 1/02* (2018.01); *A61Q 11/00* (2013.01); *A61K 2800/882* (2013.01)

(58) Field of Classification Search
None
See application file for complete search history.

(56) References Cited

U.S. PATENT DOCUMENTS

| 4,743,229 | A | 5/1988 | Chu |
|---|---|---|---|
| 4,994,029 | A | 2/1991 | Rohrbough |
| 5,997,764 | A * | 12/1999 | Ambuter .................. C11D 3/16 252/186.25 |
| 6,234,196 | B1 | 5/2001 | Fischer et al. |
| 6,582,681 | B1 | 6/2003 | Bornstein |
| 2002/0055708 | A1 | 5/2002 | Peterson |
| 2005/0118115 | A1 | 6/2005 | Fontenot |
| 2007/0111911 | A1 * | 5/2007 | Rogozinski ............ A01N 59/00 510/130 |
| 2009/0324662 | A1 | 12/2009 | Kutsch et al. |
| 2012/0164235 | A1 | 6/2012 | Northey |
| 2013/0216487 | A1 | 8/2013 | Lee et al. |

FOREIGN PATENT DOCUMENTS

WO   2014-118090 A1   8/2014

OTHER PUBLICATIONS

Sep. 26, 2016 International Search Report submitted in International Patent Application No. PCT/EP2016/063839.

* cited by examiner

Primary Examiner — Nannette Holloman
(74) Attorney, Agent, or Firm — Oliff PLC

(57) ABSTRACT

A two-component system for the preparation of a hydrogel for preventing and/or treating a periodontal disease, selected from the group consisting of periimplantitis, gingivitis, periodontitis and peri-implant mucositis. The two-component system comprises as a first component an aqueous suspension having a pH value of less than 7 comprising a pH-sensitive gelling agent, and as a second component a sodium hypochlorite (NaOCl) solution at a pH in the range of 10 to 13. The first component is physically separated from the second component.

17 Claims, 9 Drawing Sheets

TWO-COMPONENT SYSTEM

Figure 1:
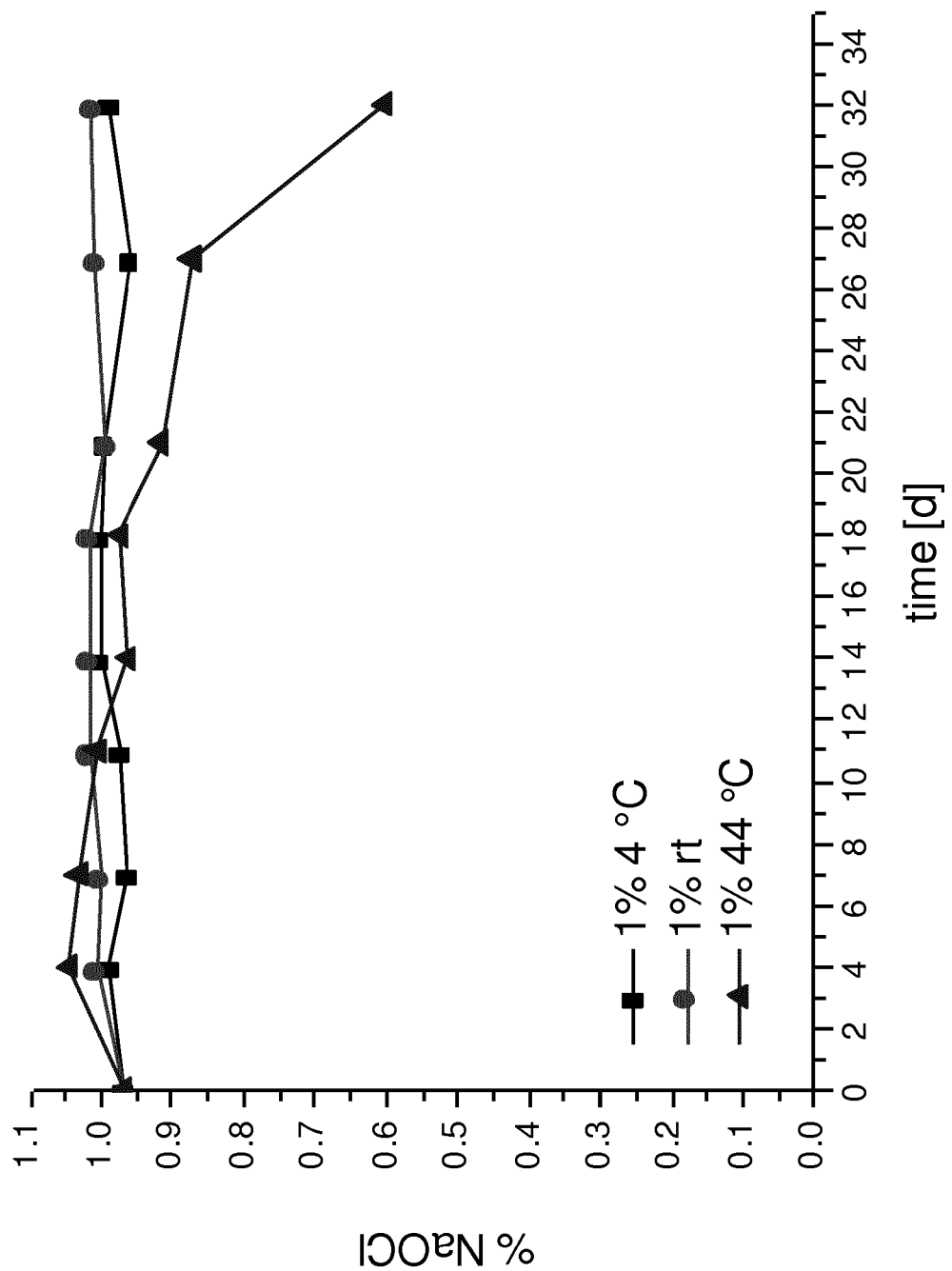

The present invention relates to two-component system for the preparation of a hydrogel for preventing and/or treating a periodontal disease and, more particularly, to a hydrogel suitable for topical application to prevent and/or treat periodontitis and/or periimplantitis.

Periodontal disease is the major cause of tooth loss in adults. The periodontium is subject to inflammation for many reasons, primary among them being the accumulation of plaque deposits under and above the gum line. These calcareous deposits of organic and mineral matter, which consist of microbial colonies growing in carbohydrate residues from food, attach themselves to tooth surfaces and can, over time, calcify into dental calculus. This hard, mineralized substance adheres tenaciously to the teeth and, when under the gum line, causes inflammation of the periodontium. Other causes of periodontitis can include malocclusion, food impaction and mouth breathing.

Treatment of periodontal diseases usually involves the removal of bacterial deposits and dental calculus. However, it is difficult to have full access for treating deeper periodontal pockets, resulting in remaining bacteria that may re-infect the tissue. This is of course also the case for other bacterially infected tissues, where an incomplete removal of bacteria or dead or damaged tissue may cause problems for healing and give rise to re-infection. Therefore, this treatment is often combined with surgical procedures to open the periodontal pocket. The area in then scraped or otherwise mechanically freed from bacterial deposits and calculus but also granulation tissue and bacterial toxin.

US 2013/0216487 discloses a teeth-whitening gel comprising a halogenated polypeptide made of a polyglutamic acid and sodium hypochlorite.

US 2012/0164235 discloses a hydrogel formulation containing an oxidative reduction potential water solution and a gelling agent.

US 2005/0118115 discloses a method for whitening the teeth, wherein the primer is applied to the surface of the tooth, after which a peroxide tooth whitening composition is delivered and applied to the teeth.

US 2009/0324662 discloses a product for reducing dental disease in a patient comprising a carrier and an anti-dental disease agent with a pH above 7.0.

U.S. Pat. No. 6,582,681 discloses a method and a preparation of cleaning tooth root surfaces and surrounding tissue. Said preparation comprises a gel substance and hypochlorite. As possible gel substance carboxy methyl cellulose (CMC) is mentioned. CMC produces stables gels in a very broad pH range. However, the mixture of the gel and the hypochlorite is in practice rather difficult or it has to be carried out at a pH higher than 10, since at this pH the viscosity of the gel decreases. But, such a high pH of the final preparation can damage the soft tissue. Chlorhexidine is a potent antiseptic, which is widely used for chemical plaque control in the oral cavity. Aqueous solutions of 0.1 to 0.2% are recommended for that purpose, while 2% is the concentration of root canal irrigating solutions usually found in the endodontic literature.

Due to its wide-spectrum, nonspecific killing efficacy on all microbes, aqueous sodium hypochlorite is used in endodontics as main irrigant. In addition, sodium hypochlorite solutions (NaOCl) are cheap and easily available. However, the inherent instability of sodium hypochlorite is a major challenge. In order to not reduce the already limited shelf life, a sodium hypochlorite solution is optimally kept at a strongly basic pH, at a low concentration in the dark at low temperatures. In addition, the best antimicrobial activity is reached at a neutral pH.

Due to the efficiency of these two compositions it is desirable to combine said components. However, the combination of sodium hypochlorite and chlorhexidine forms an orange-brown precipitate. Such an orange-brown precipitate is highly unwanted, especially in the visible area of the mouth. In WO 2014/118090 a kit of parts for treating a periodontal disease is disclosed comprising 0.01 to 1% by weight sodium hypochlorite (NaOCl) solution and 0.01 to 1% by weight chlorhexidine (CHX) solution and instructions for a sequential administration to a site of microbial infection in a patient so that the sodium hypochlorite solution is to be administered before the chlorhexidine solution. However, despite being in compliance with the instructions an unwanted distribution of the sodium hypochlorite solution in the mouth may occur which, if not detected, may result in the orange-brown precipitate when applying the chlorhexidine solution.

Therefore, it is an object of the present invention to provide a composition for the treatment of periodontal disease, which allows a precise application at the site of infection.

The problem is solved by a two-component system according to claim 1. Further preferred embodiments are subject of the dependent claims.

Surprisingly, it was found that a two-component system for preventing and/or treating a periodontal disease comprising a) as a first component an aqueous suspension having a pH value of less than 7 comprising at least one pH-sensitive gelling agent, and b) as a second component a sodium hypochlorite (NaOCl) solution at a pH in the range of 10 to 13, wherein the first component is physically separated from the second component, allows the in situ preparation of a stable hydrogel comprising sodium hypochlorite. Said hydrogel has a final pH in the range of 6 to 9.5. Said pH range enhances the antimicrobial activity of the sodium hypochlorite. Due to the fact, that aqueous suspension of the first component has a pH value of less than 7 and the solution in the second component has a pH in the range of 10 to 13 it is possible to obtain a hydrogel having a pH in the desired range. The hydrogel resulting from the two-component system according to the present invention allows to prevent an unwanted distribution of the sodium hypochlorite solution in the mouth. In addition, the two-component system according to the present invention has a good long term stability, since it overcomes the problem that NaOCl is relatively instable at neutral pH, which is highly desirable in terms of quality control and reproducibility of a medical product.

Due to the presence of the hydrogel, a precise application of the sodium hypochlorite at the infected location is possible. In addition, the adherence of the hydrogel results in a longer presence of the sodium hypochlorite. Furthermore, due to the immobility of the sodium hypochlorite, the concentration is high at the site of infection for a longer time.

Due to the salt lability of the gelling agent in the gel, the gel can be removed by rinsing the mouth with a saline solution such as an isotonic solution. Therefore, the dentist can keep the hydrogel localized at the site of infection for, for example, 0.5 to 5 minutes, preferably 1 to 2 minutes, before dissolving the hydrogel by rinsing with an isotonic solution.

Within the context of the present invention, a periodontal disease is a serious gum infection that damages the soft tissue and destroys the bone that holds the teeth. The periodontal disease is preferably selected from the group consisting of periimplantitis, gingivitis, periodontitis and peri-implant mucositis.

The expression pH-sensitive gelling agent stands for a polymer comprising acidic groups, such as carboxylic or sulfonic acids, which either accept or release protons in response to changes in environmental pH. Preferably, the pH-sensitive gelling agents comprise acidic groups selected from the group consisting of carboxylic or sulfonic acids or a mixture thereof. The presence of ionizable groups on such a polymer results in swelling of the hydrogels much beyond that can be achievable by non-electrolyte polymer hydrogels. Since the swelling of such a hydrogel is mainly due to the electrostatic repulsion among charges present on the polymer chain, the extent of swelling is influenced by any condition that reduce the electrostatic repulsion. Therefore, hydrogels made of a pH-sensitive gelling agent are also sensitive to ionic solutions, such as an isotonic salt solution.

In the two-component system according to the present invention the pH-sensitive gelling agent is in an aqueous suspension. The suspension is in liquid form. In other words, the pH of the suspension is chosen such that no gelling occurs. Typically, the pH of the suspension in the first compartment is less than 7, preferably less than 5, most preferably less than 4, even more preferably between pH 1 to 3.5, ideally between pH 2 and 3.5. The later pH range is optimal, since it provides a good viscosity behavior in a broad temperature range as well as an optimal pH of the final hydrogel. In the context of the present invention a viscosity of less than 4000 mPa*s at 20° C. is considered as liquid, and a viscosity of more than 40000 mPa*s at 20° C. is considered to be a gel. A viscosity of 4000 to 40000 mPa*s at 20° C. is acceptable for the aqueous suspension comprising the pH-sensitive gelling agent, however, a viscosity of less than 4000 mPa*s at 20° C. is preferred, since it allows a particularly good handling of the aqueous suspension. Most preferably the aqueous suspension comprising the pH-sensitive gelling agent has a viscosity of less than 1500 mPa*s at 20° C. The viscosity is measured by using a Brookfield Viscometer at 20° C. according to the lubrizol test procedure TP-AATM-105A-b (Edition of 12 Oct. 2006).

A treatment with a hydrogel obtained by mixing the two-components of the two-component system according to the present invention results in a substantive removal of subgingival pathogenic biofilm at the site of microbial infection in the patient suffering from a periodontal disease and/or in a substantive inhibition of the growth and/or regrowth of a subgingival pathogenic biofilm at the site of microbial infection in a patient suffering from a periodontal disease.

In the two-component system according to the present invention the first component is separated from the second component, which means that they are physically separated from each other and thus are not in contact with each other. Due to the separation into two different compartments the two-component system according to the present invention has a long shelf stability. First of all, the separation allows to store the sodium hypochlorite solution at high concentration and at a pH between 10 and 13, preferably between 11 and 13, and most preferably between 11 and 12, which are optimal conditions for storing a sodium hypochlorite solution. Second, a hydrogel comprising a pH-sensitive gelling agent and sodium hypochlorite would have a significantly reduced shelf life, since sodium hypochlorite is also a salt, which destabilizes the hydrogel. In addition, potential side reactions, between the pH-sensitive gelling agent and sodium hypochlorite can be avoided. In fact, the separation of the two components allows to obtain a well-defined concentration of the active substance sodium peroxide.

Preferably, the second component comprising the NaOCl solution is stored in the dark, at low temperature (for example 4° C.) in order to ensure a shelf life of about one year. If the NaOCl solution is exposed to sunlight for a short time, that is before application, it does not have an immediate effect on the concentration. Warming the solution to room temperature for a limited period is also acceptable. Furthermore, it is preferred to use a high quality sodium hypochlorite (starting solution), that is, sodium hypochlorite having a low concentration of transition metals, in particular of Ni, Co and Cu. For example, for a 10% NaOCl solution the Ni concentration is preferably less than 15 ppm, the Co concentration is preferably less than 80 ppm, and the Cu concentration is preferably less than 120 ppm.

The two-component system according to the present invention allows the preparation of the hydrogel just before application. The first compartment comprises as first component an aqueous suspension comprising a pH-sensitive gelling agent. The expression suspension means that it is a liquid and not a gel. The pH sensitive gelling agent is in an essentially soluble form in the first compartment ensuring autoclaving in an effective way. In addition, the first compartment may comprise salts to regulate the pH. In the first compartment the pH is less than 7, preferably less than 5, most preferably less than 4, even more preferably between pH 1 to 3.5, ideally between pH 2 and 3.5. The second compartment comprises the basic solution comprising the sodium hypochlorite. The mixing of the two components results in a change of the pH which induces the formation of a hydrogel. Due to the fact, that the aqueous suspension is in liquid form, a good mixing of the two components and a regular distribution of the hypochlorite can be obtained. This allows to obtain an essentially constant hypochlorite concentration in the hydrogel. The so obtained hydrogel can be directly applied to the wound in an easy and safe manner. In addition, due to its viscosity it will not be distributed in the whole mouth.

Preferably, the sodium hypochlorite solution in the second component of the two-component system according to the present invention has a concentration of 0.3 to 5% by weight, most preferably by 0.7 to 4.2% by weight, which results in a final concentration between 0.1 and 0.7% NaOCl in the final hydrogel.

Preferably, the aqueous suspension comprising the at least one pH-sensitive gelling agent in the first component of the two-component system according to the present invention has a concentration of 0.05 to 5% by weight, preferably 1 to 3% by weight, and most preferably 2 to 3% by weight based on the total weight of the suspension.

Preferably, the pH sensitive gelling agent in the first component of the two-component system according to the present invention is a crosslinked polyacrylic acid. Preferably the polyacrylic acid is a homopolymer of acrylic acid crosslinked with an allyl ether of pentaerythritol, allyl ether sucrose, propylene, polyalkelyether or divinyl glycol. Acrylates/$C_{10-30}$ alkyl acrylate crosspolymers are copolymers of $C_{10-30}$ alkyl acrylates and one or more monomers of acrylic acid, methacrylic acid or their simple esters thereof crosslinked with an allyl ether of sucrose or pentaerythritol. The designation "$C_{10-30}$" refers to 10 to 30 carbon atoms.

Carbopol is the tradename of a high molecular weight polymer of a crosslinked polyacrylic acid which is available from Lubrizol Corporation and is a preferred pH-sensitive gelling agent. At acidic pH the polymer is uncharged whereas at neutral pH the acid groups are deprotonated and result in a negatively charged polymer. The anionic form of the polymer has the ability to absorb and retain water and swell to many times of their original volume thereby forming a hydrogel. Examples of suitable pH-sensitive gelling agents include Carbopol 934, 934P, 940, 941, 954, 980, 981, 1342, 1382, 2984, and 5984; Aqua SF-1 polymer; and Carbopol ETD 2001 and ETD 2050; and Carbopol Ultrez 10. Carbopol 974 and 980 and are most preferred carbomers in the present invention. Acrylates/$C_{10-30}$ alkyl acrylate crosspolymers are also available from Noveon Incorporated under the tradename Pemulen TR1 or TR2, Carbopol 1342 or 1382, Carbopol ETD 2020, and Carbopol Ultrez 20 and 21. Carbopol ETD 2020 is the most preferred acrylate/$C_{10-30}$ alkyl acrylate crosslinked polyacrylic acid.

Water is preferably present in the suspension comprising the pH sensitive gelling agent in an amount from 90 to 99.5% by weight, more preferably in an amount from 95 to 99.5% by weight, and most preferably in an amount from 97 to 99% by weight, based on the total weight of the suspension.

Two-component system according to the present invention comprises preferably a non-toxic pH sensitive or oxidation sensitive colorant. Said colorant may be either in the aqueous solution comprising the pH-sensitive gelling agent or in the sodium hypochlorite solution. The non-toxic pH sensitive or oxidation sensitive colorant allows to monitor the mixing of the two components. Most preferably, it is in the aqueous suspension comprising the pH-sensitive gelling agent. In the context of the present invention a non-toxic pH sensitive colorant is an indicator which causes the color of the solution to change depending on the pH, and which has in the used concentration no toxic effect on humans. In the context of the present invention a non-toxic oxidation sensitive colorant is an indicator which causes the color of the solution to change depending on its oxidation, and which has in the used concentration no toxic effect on humans. Preferably, such a non-toxic pH sensitive or oxidation sensitive colorant is selected from the group consisting of methylene blue, indigocarmine, methyl green, bromocresol green, sodium alizarine sulphonate, chlorophenol red, bromthymol purple, bromthymol blue, azolitmin, neutral red, cyanine, phenol red, cresol red, thymol blue, α-Na phenolphthaleine, phenolphthaleine, α-Na phthalein, thymolphtaleine, nile blue, alizarine yellow, methyl violet, methyl yellow, bromphenol blue, paranitrophenol, bromphenol purple and litmus, most preferably methylene blue and litmus.

In a most preferred embodiment of the present invention the first component comprising the pH-sensitive gelling agent additionally comprises methylene blue. Upon mixing with the second component, that is, with the sodium hypochlorite solution having a pH in the range of 10 to 13, preferably 11 to 13, a change of a color can be observed, indicating a complete mixture of the two components.

Preferably, the system of the two-component system is a dual cartridge or a dual syringe. Such systems are known to those skilled in the art. For example U.S. Pat. Nos. 5,116, 315, 4,735,616, 6,328,229 or U.S. Pat. No. 2002/0042591 disclose mixing arrangements in which the components which are contained in two syringes are discharged together through a mixer and mixed in the process. Furthermore, it is known to connect two syringes to one another at their ends so that the components which are contained in the syringes can be thoroughly mixed by backward and forward transfer. Such arrangements are known, for example, from U.S. Pat. Nos. 4,743,229, 4,994,029, 6,234,196 or U.S. Pat. No. 2002/0055708.

By mixing the first and the second component of the two-component system a hydrogel is obtained having a pH in the range of 6.0 to 9.5, preferably 6.0 to 8.5, and most preferably 6.5 to 7.5. It was found that in particular in a pH range of 6.5 to 7.5 optimal antimicrobial activity of the sodium hypochlorite could be obtained.

The final hydrogel has preferably a sodium hypochlorite concentration of 0.005 to 6% by weight, most preferably 0.1 to 2.0% and ideally 0.1 to 0.5% by weight based on the total weight of the hydrogel. Preferably, for endodontic treatments the final hydrogel has a higher sodium hypochlorite concentration, that is, in the range between and 6%, whereas for application which involve direct contact with living tissue the final hydrogel has a lower sodium hypochlorite concentration, that is, in the range between 0.1 and 2% by weight.

Preferably, after removal of the hydrogel by rinsing with a saline solution, the site of infection is subsequently treated with a composition comprising chlorhexidine. Said composition comprising chlorhexidine may either be an aqueous solution or a hydrogel as well. Accordingly, the present invention also relates to a kit of parts comprising a two-component system according to the present invention and a composition comprising chlorhexidine.

Preferably, the composition comprising chlorhexidine is an aqueous solution or a hydrogel. Chlorhexidine tends to stick to the tissues and thus stays at the site long and shows a long-term effect. Therefore, preferably, the treatment with the hydrogel obtained by mixing two-component systems according to the present invention is preferably followed by a treatment of chlorhexidine.

In one embodiment of the kit of parts, the composition comprising the chlorhexidine is a gel. Such a hydrogel can be prepared in situ as well by another two-component system comprising as a first component an aqueous suspension comprising a pH sensitive gelling agent, and a chlorhexidine solution having a pH with is above the gelling pH of the gelling agent, that is the pH above which a hydrogel is formed. Due to the in situ preparation of the hydrogel according to the present invention the addition of a humectant such as glycerin and other polyols can be avoided. Therefore, it is possible to obtain a glycerin-free hydrogel. Since there is a significant number of patients who do not want to be treated with a product containing glycerin derived from animal and since glycerin derived from plants is rather expensive, formulations being free from glycerin are preferred.

The present invention also relates to a method for treating a periodontal disease selected from the group consisting of periimplantitis, gingivitis, periodontitis and periimplant mucositis. Said method typically involves the following steps:
  mechanically cleaning and/or debriding the site of microbial infection;
  cleaning and/or disinfecting the site of microbial infection with a hydrogel comprising a sodium hypochlorite solution, whereby said hydrogel is obtained by mixing the two components of the two-component system according to the present invention;
  rinsing the site of the microbial infection with a saline solution;
  optionally cleaning and or disinfecting the site of microbial infection with a hydrogel comprising a chlorhexidine solution;

optionally rinsing the site of microbial infection with a saline solution.

The first step relating to the mechanical cleaning of the site of infection can be carried out with a mechanical cleaning and/or debridement tool, which is preferably selected from the group consisting of a cuvette, a drill, a brush, an ultrasonic device and a spatula. In case of a titanium implant, the mechanically cleaning is most preferably carried out with a titanium-bristled brush.

In the second step, the hydrogel is prepared by mixing the two components of the two-component system according to the present invention. Directly after preparing the hydrogel the site of microbial infection is cleaned and/or disinfected by the sodium hypochlorite which is contained in the hydrogel.

In the third step, the site of the microbial infection is treated with a saline solution which results in the degradation of the hydrogel. Accordingly, the hydrogel can be removed easily. In addition, since the hydrogel is particularly sensitive to salts and, thus its removal by saline solution is very effective, a colored precipitate from reaction of CHX with NaOCl is effectively prevented.

In an optional forth step, the site of microbial infection is treated with a chlorhexidine solution or gel, which may be removed by rinsing with a saline solution as well or may stay in place.

The hydrogel according to the present invention may be used for preventing and/or treating a periodontal disease, which is preferably selected from the group consisting of periimplantitis, gingivitis, periodontitis, and peri-mucositis.

EXAMPLES

Materials:

Carbopol 974P NF (Lubrizol, CBP1053), Carbopol ETD 2020 NF (Lubrizol, CBP1070A), Carbopol 980 NF (Lubrizol, CBP1055A), $NaOCl_{aq}$ (10-15%, Sigma, 425044-250 mL), NaOH (Sigma-Aldrich, 55881-500 g), methylene blue (Roth, A5141). Titrations were carried out with a 974 Basic titrino (Metrohm, QS52031) with a Pt-electrode (Metrohm, 6.0309.100). The viscosity was measured with a rheometer (Anton Paar, MCR 300, QS52026). pH was measured with a 780 pH Meter (Metrohm, electrode: 6.0258.600). Samples were stirred with a mechanical stirrer (Heidolph, R Z R 2021 or RZR 2102 control). The samples were sterilised with an autoclave (Systec, 2540 EL) or by gamma-irradiation, which was done externally (Früh Verpackungstechnik AG, 25-42 kGy).

LEGEND OF THE FIGURES

FIG. 1: A 1% NaOCl solution was stored at 4° C., room temperature and 44° C. Over the period of 1 month only the sample stored at 44° C. showed a decrease in concentration.

Figure 2:
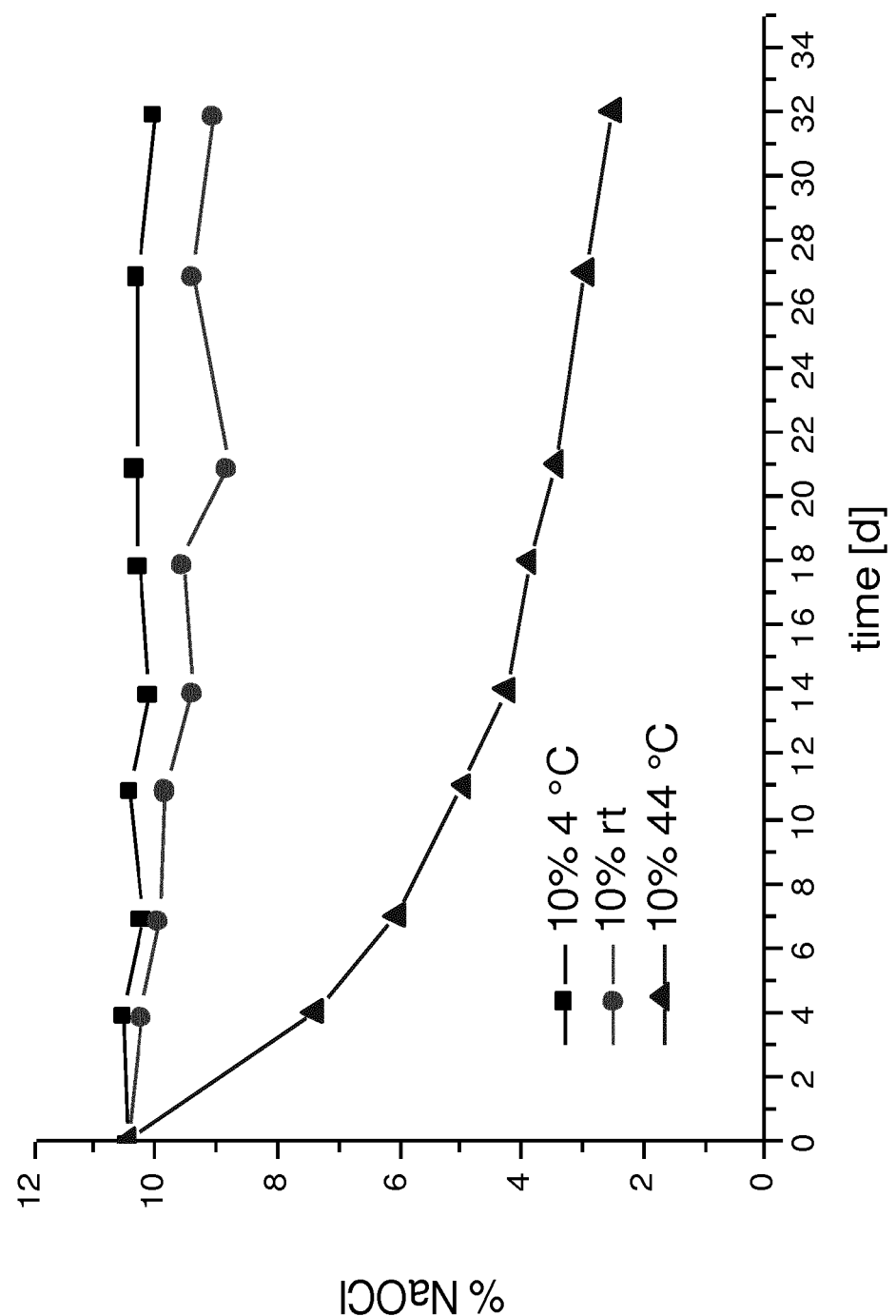

FIG. 2: A 5% NaOCl solution was stored at 4° C., room temperature and 44° C. Over the period of 1 month no significant difference in concentration for the samples at 4° C. and room temperature was observed. The sample at 44° C. showed a loss of concentration of about 40%.

Figure 3:
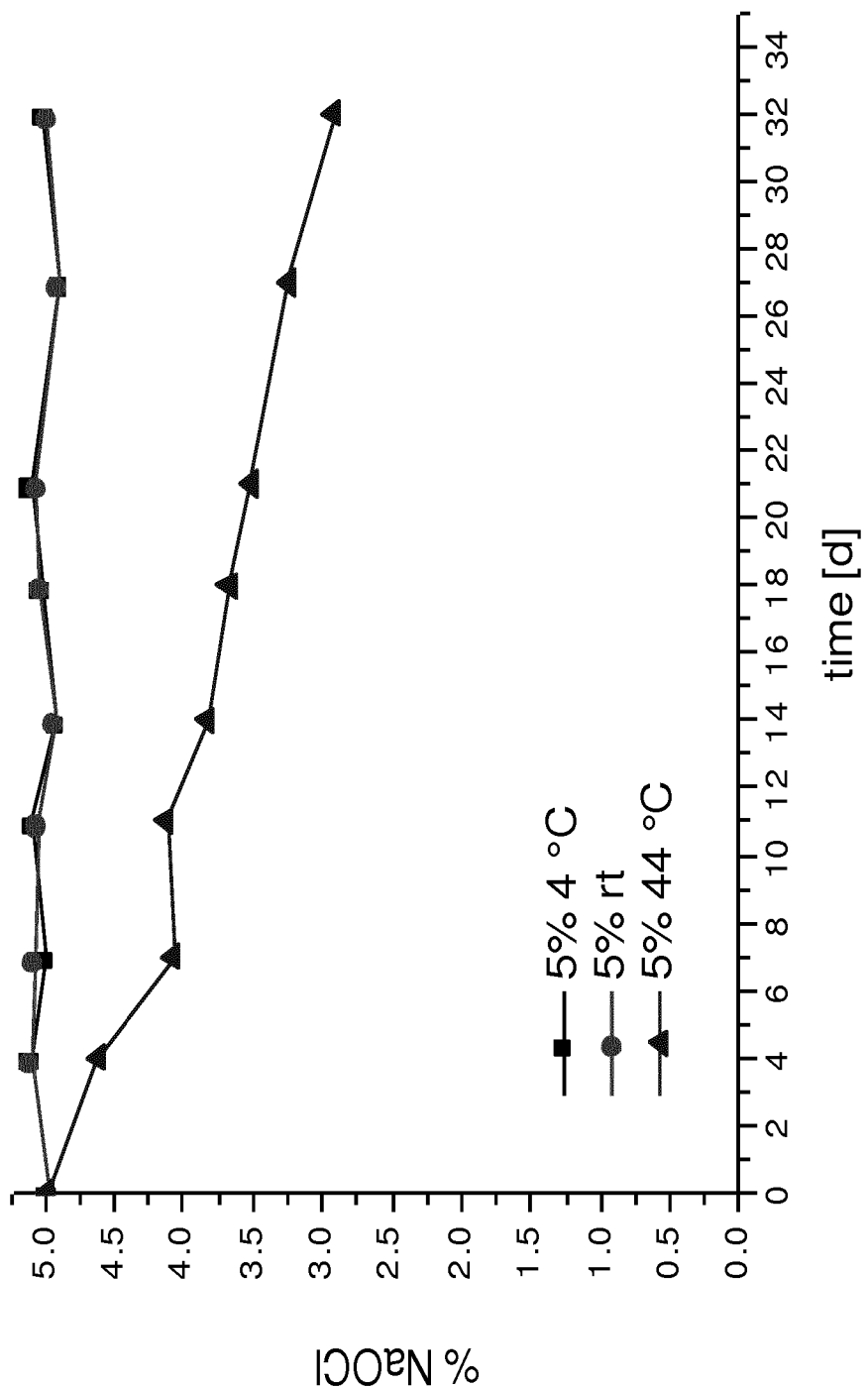

FIG. 3: A 10% NaOCl solution was stored at 4° C., room temperature and 44° C. Over the period of 1 month no significant difference in concentration for the samples at 4° C. and room temperature was observed. The sample at 44° C. showed a decrease in concentration of over 70%.

Figure 4:
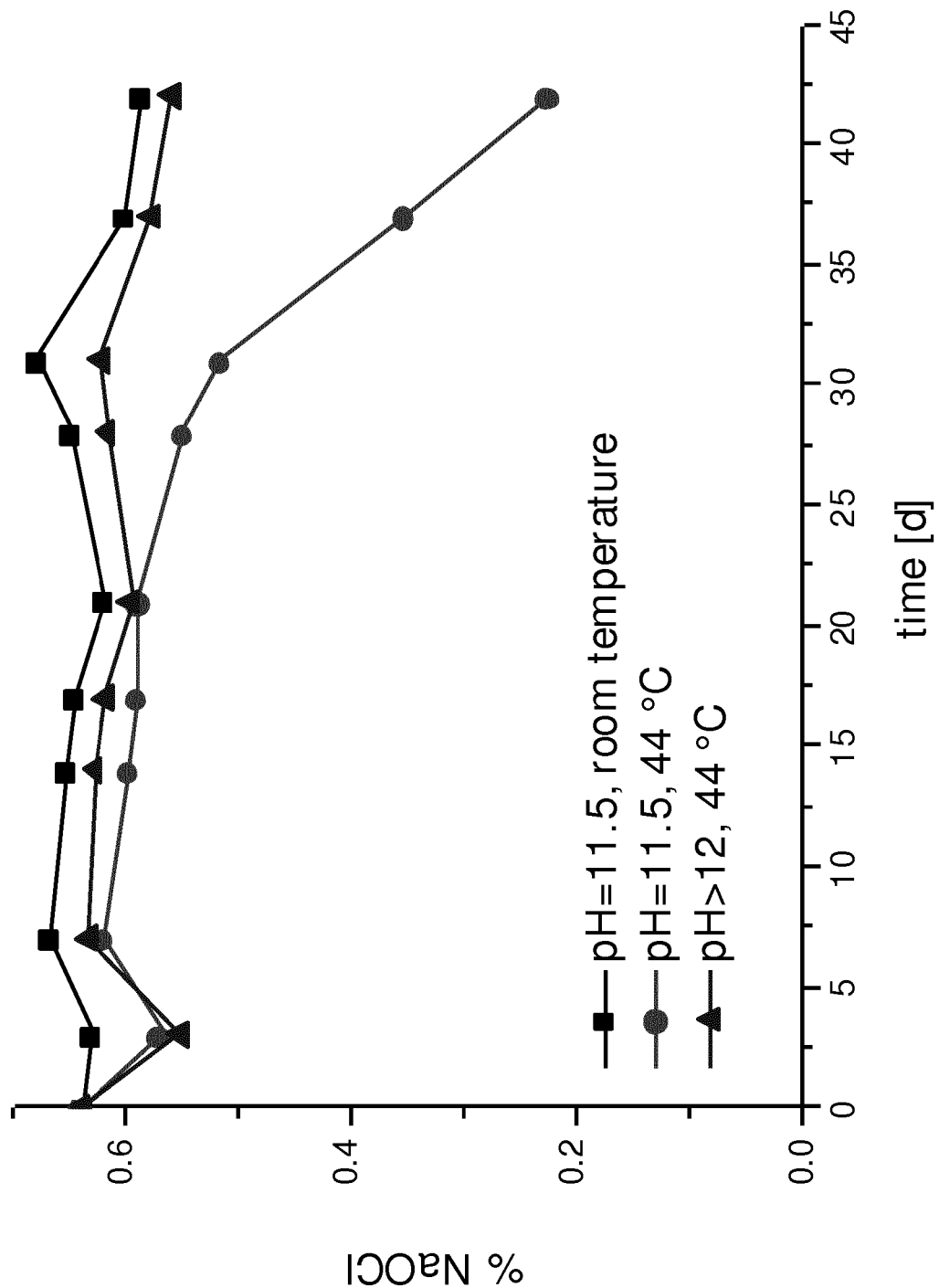

FIG. 4: 0.6% NaOCl solution stored at r.t., pH=11.4 and exposed to sunlight (square), stored at 44° C., pH=11.5 (circle) and >12 (triangle) in the dark.

Figure 5:
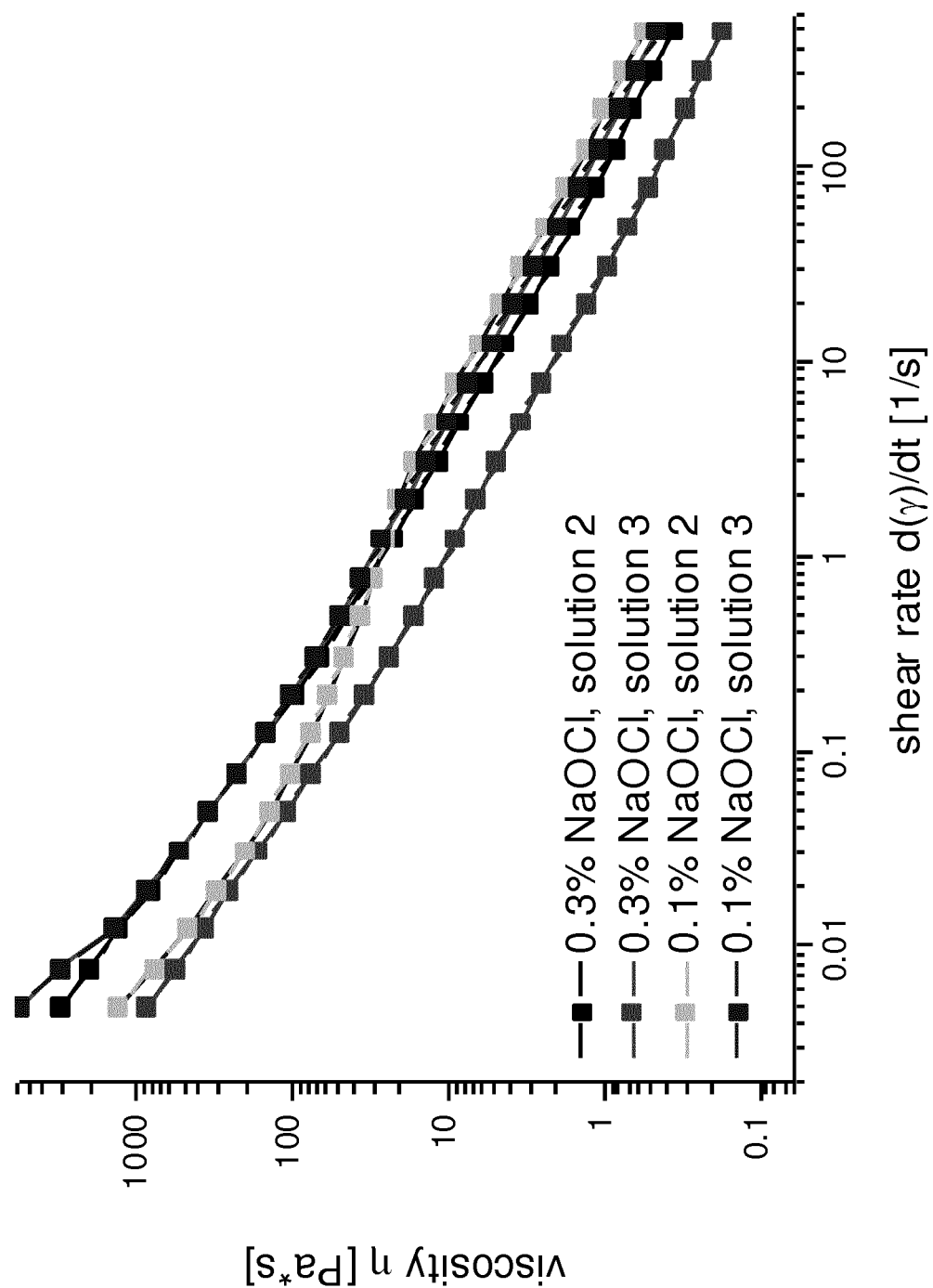

FIG. 5: Viscosity measurement of the 4 promising combinations. All samples were prepared and measured twice and the mean value is displayed here. The higher the dilution and the lower the NaOCl concentration, the lower is the viscosity.

Figure 6:
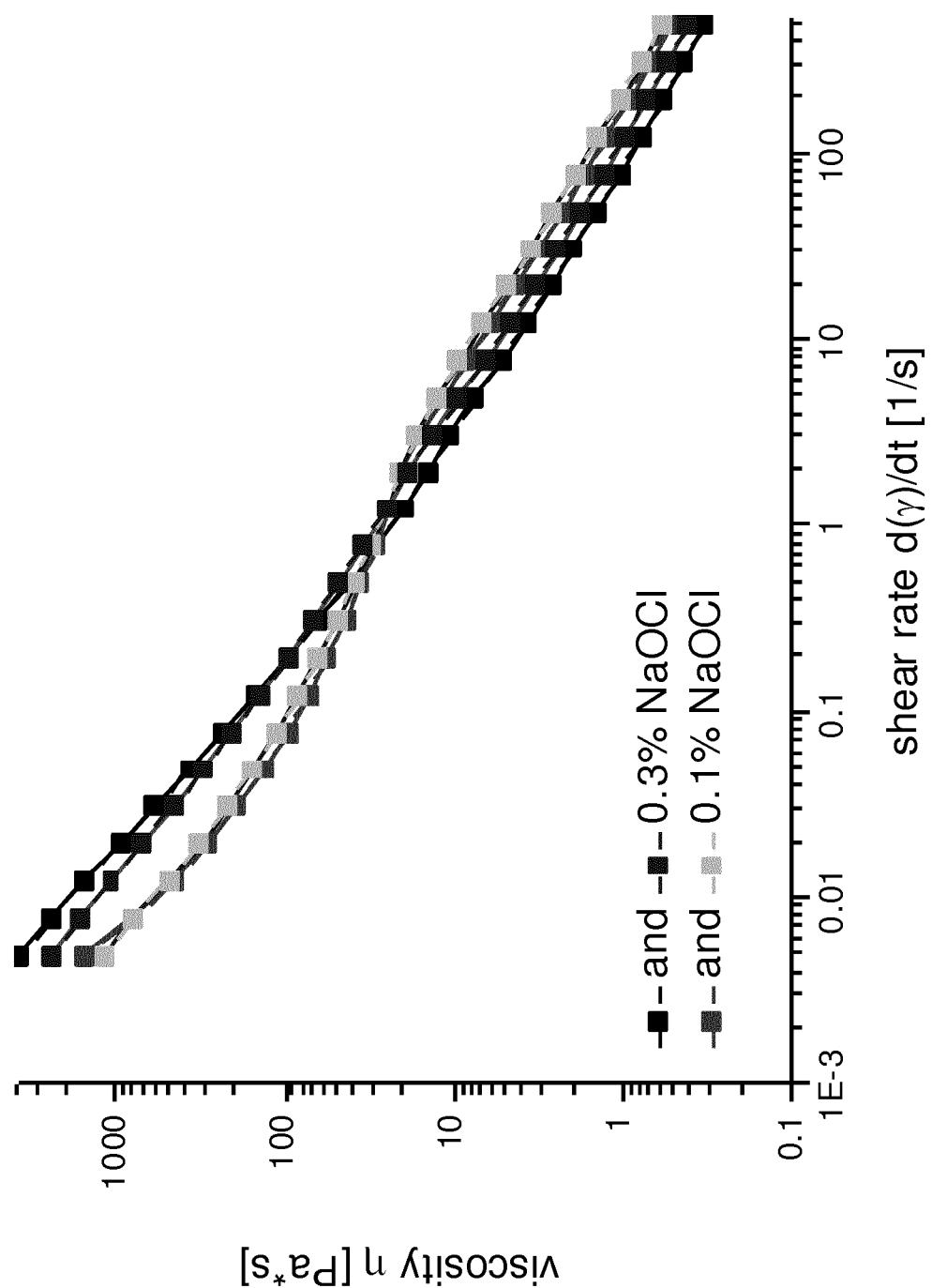

FIG. 6: Comparison between 2% Carbopol with a final NaOCl concentration of 0.1% and 0.3% mixed with solution 2 (0.4 g). Both samples were mixed and measured twice to investigate the experiment's reproducibility.

Figure 7:
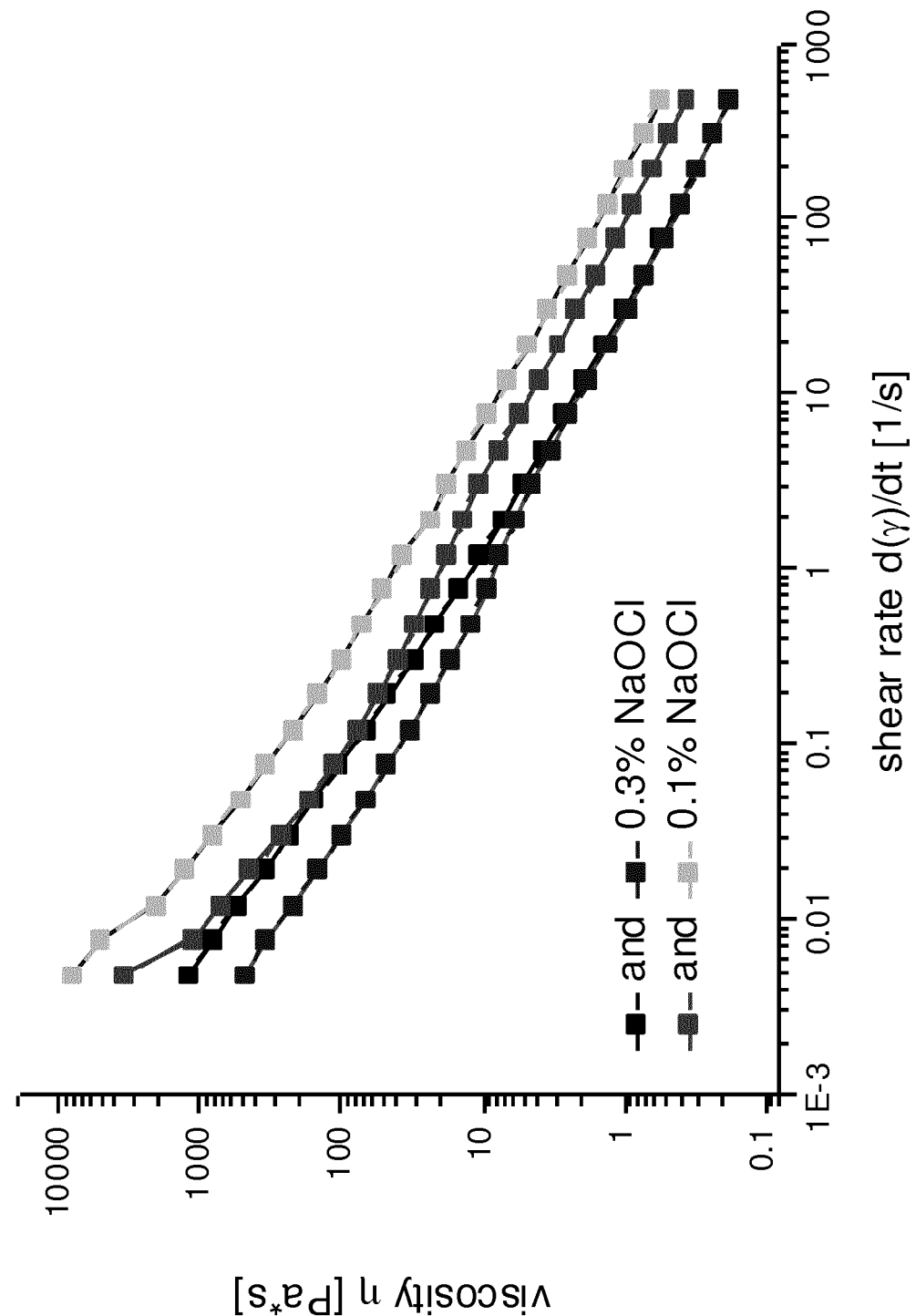

FIG. 7: Comparison between 2% Carbopol with a final NaOCl concentration of 0.1% and 0.3% mixed with solution 3 (0.8 g). Both samples were mixed and measured twice to investigate the experiments reproducibility.

Figure 8:
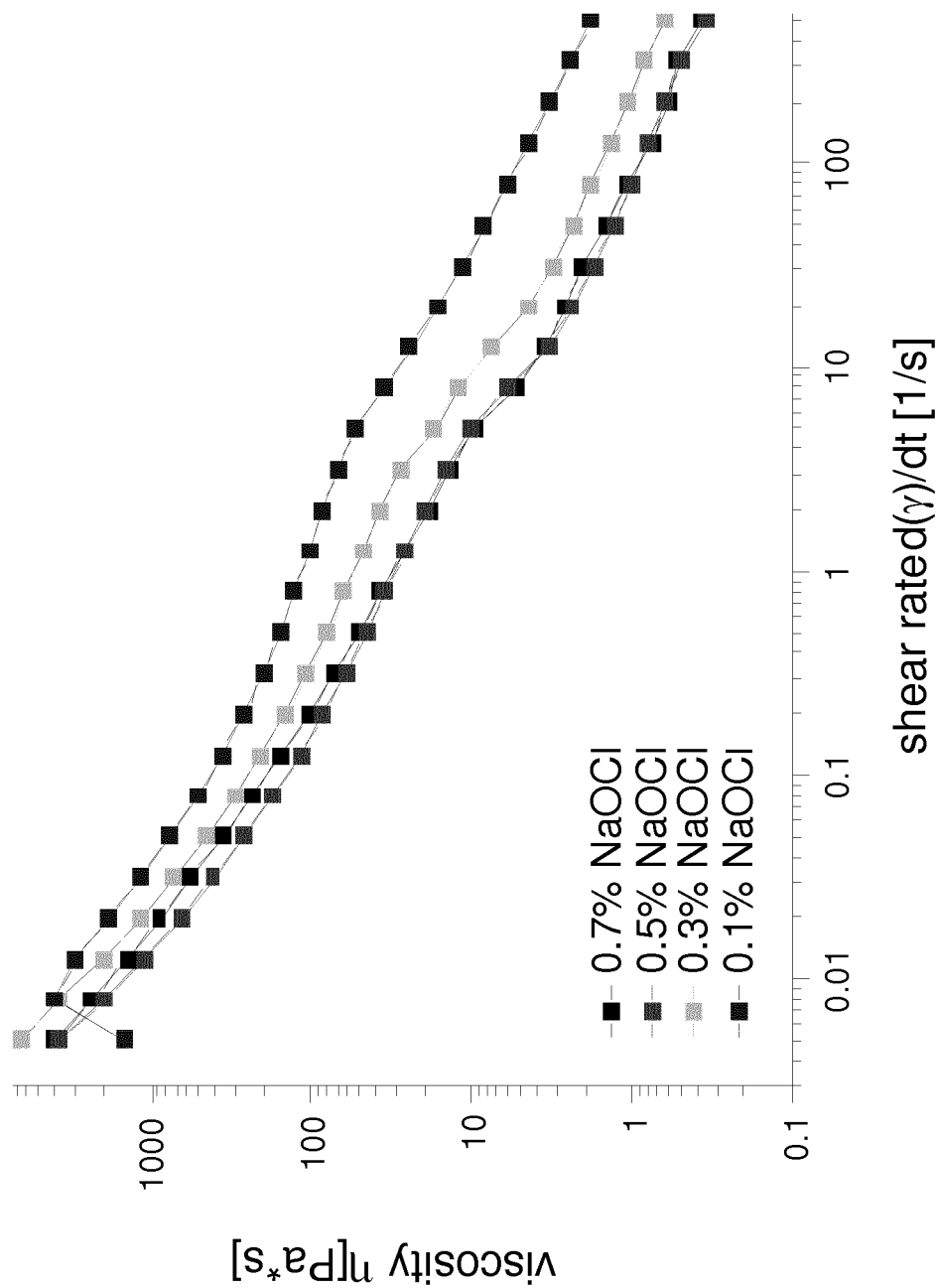

FIG. 8: Effect of NaOCl concentration on the viscosity of 1.5% Carbopol ETD 2020 N F. The higher the hypochlorite concentration, the more liquid is the sample.

Figure 9:
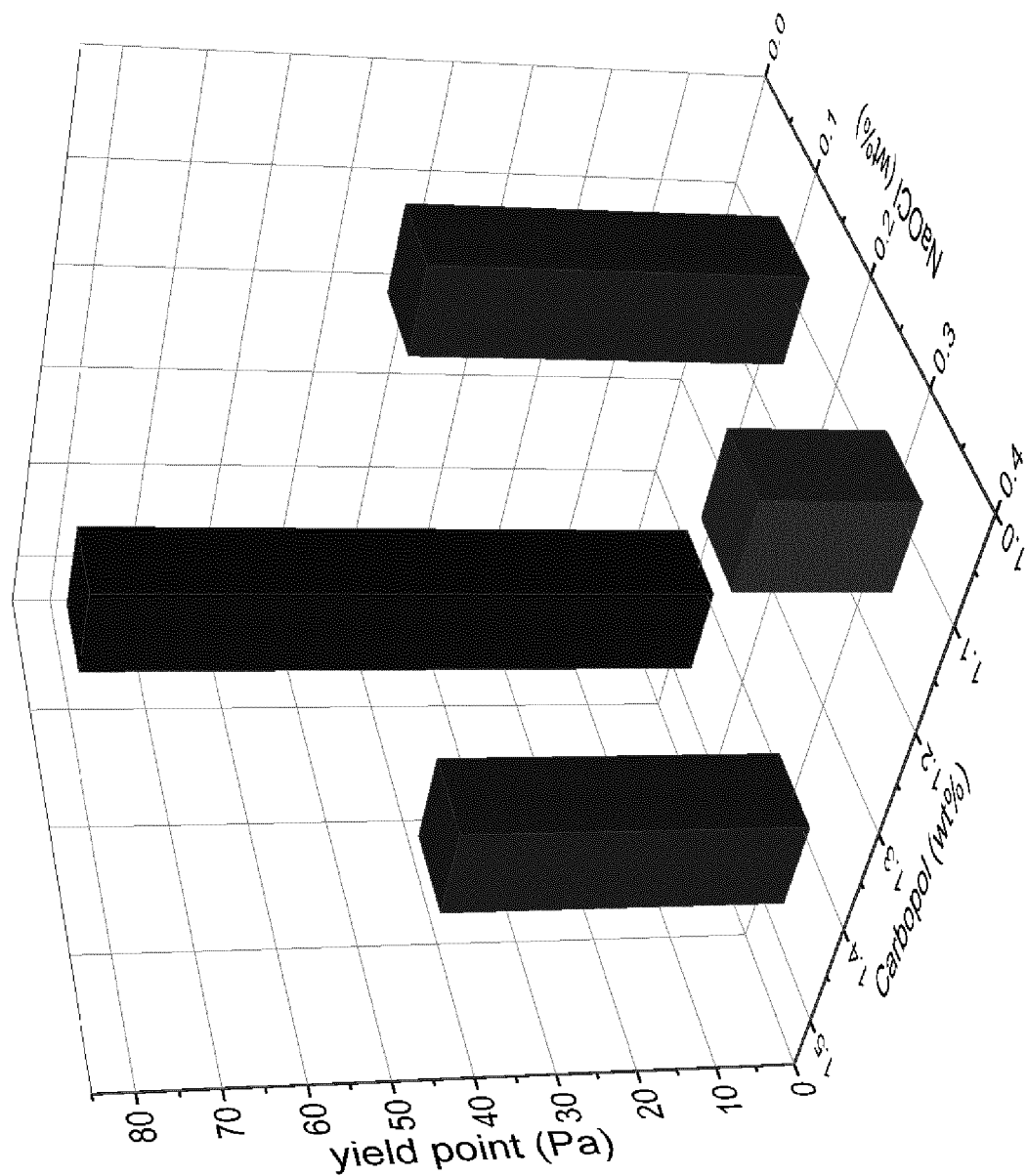

FIG. 9: Yield point measurements of 2% Carbopol 975P NF (1.0 g) mixed with solution 2 (0.4 g) or solution 3 (0.8 g) with a final NaOCl concentration of 0.1% or 0.3%. The higher the NaOCl content and the lower the final Carbopol concentration the lower is the yield point.

PREPARATION OF CARBOPOL GEL

Example: Carbopol 974P NF Polymer

1%, 2% and 3% Carbopol 974P NF suspensions have been prepared. Methylene blue (4 mg) was dissolved in reverse Osmosis $H_2O$ (300 mL, MilliQ) which resulted in a blue coloured solution. This solution (99 g) in a 250-mL-beaker was placed under the mechanical stirrer with a ringed propeller under a slight angle (ca. 10-20°). Carbopol 974P NF polymer (1 g) was added while stirring at 400 rpm and stirring was continued for 90 min or until no lumps were visible anymore. The suspension was filled in two 50-mL-falcon tubes.

TABLE 1

Preparation of the 1%, 2% and 3% Carbopol 974P NF suspensions used in the two component system.

|  | $H_2O$ | Carbopol |
| --- | --- | --- |
| 1% Carbopol 974P NF | 99 g | 1.0 g |
| 2% Carbopol 974P NF | 98 g | 2.0 g |
| 3% Carbopol 974P NF | 97 g | 3.0 g |

Preparation of Basic Solutions

Example: Solution 2 for 0.3% NaOCl Final Concentration $NaOH_{aq}$ (1 M, 10 mL), reverse osmosis $H_2O$ (10 mL) and $NaOCl_{aq}$ (10%, 2 mL) were mixed. pH and NaOCl concentration were measured. For each experiment 4 solutions were prepared (see Table 2).

TABLE 2

Preparation of the 4 solutions for final NaOCl
concentrations of 0.7%, 0.3% and 0.1%.

|  | 1M NaOH$_{aq}$ | 0.1M NaOH$_{aq}$ | H$_2$O | 10% NaOCl$_{aq}$ | [NaOH] in solution[a] | [NaOCL] in solution[b] |
|---|---|---|---|---|---|---|
| final concentration: 0.7% NaOCl ||||||| 
| Solution 1 | 7.0 mL | — | — | 5.0 mL | 1 M | 4.17% |
| Solution 2 | 10.0 mL | — | 10.0 mL | 7.0 mL | 0.5 M | 2.59% |
| Solution 3 | 3.8 mL | — | 11.2 mL | 3.0 mL | 0.25 M | 1.67% |
| Solution 4 | — | 7.0 mL | — | 0.8 mL | 0.1 M | 1.03% |
| final concentration: 0.3% NaOCl |||||||
| Solution 1 | 8.0 mL | — | — | 2.0 mL | 1 M | 2.00% |
| Solution 2 | 10.0 mL | — | 10.0 mL | 2.5 mL | 0.5 M | 1.11% |
| Solution 3 | 3.8 mL | — | 11.2 mL | 1.2 mL | 0.25 M | 0.74% |
| Solution 4 | — | 8.0 mL | — | 0.4 mL | 0.1 M | 0.48% |
| final concentration: 0.1% NaOCl |||||||
| Solution 1 | 9.0 mL | — | — | 0.7 mL | 1 M | 0.763% |
| Solution 2 | 10.0 mL | — | 10.0 mL | 0.8 mL | 0.5 M | 0.428% |
| Solution 3 | 3.8 mL | — | 11.2 mL | 0.4 mL | 0.25 M | 0.265% |
| Solution 4 | — | 10.0 mL | — | 0.2 mL | 0.1 M | 0.213% |

[a] not including the NaOH contained in the NaOCl solution
[b] x mL 10% NaOCl$_{aq}$/(y mL NaOH$_{aq}$ + z mL H$_2$O + x mL 10% NaOCl$_{aq}$)

Syringes and Mixing

The Carbopol 974P NF polymer suspension (1 g) and solutions 1 (0.2 g, Table 2), 2 (0.4 g), 3 (0.8 g) and 4 (2 g) were each weighed into 2-mL-syringes with Luer lock. The connector was fixed between two syringes (one containing polymer, the other one of the solutions) and the two components were mixed until the blue colour was not visible anymore. After mixing, the NaOCl concentration was determined by titration. The viscosity, yield point and pH were measured for a number of representative samples.

Titrations

The NaOCl concentration was determined by iodometric titration. The samples were measured one to three times (see Table 8).

Rheological Measurements

Ca. 300 µL of the hydrogel were placed on the Peltier element (25° C.), the cone (diameter: 24.952 mm, angle: 2.009°, truncation: 51 µm) was lowered to d=0.105 mm and excess material was removed with a spatula. Water droplets were placed around the stamp and the temperature hub was lowered. Then, preshear of d(γ)/dt=50 1/s was briefly applied, the sample was allowed to rest for 10 min, and a shear rate sweep from d(γ)/dt=0.005 to 500 1/s was started.

Subsequently, the yield point, i.e. the stress at which the sample begins to deform, was determined for a number of representative samples.

Quality of the Starting Solution with Regard to Metals

Despite the fact, that the shelf life of NaOCl is short and may be influenced by several factors (e.g. temperature, pH, light, concentration and presence of transition metals), it was found, that a high quality could be reached. As the quality of the NaOCl is important, the amount of transition metals was analysed by elemental analysis (Table 3).

TABLE 3

Result of elemental analyses of two NaOCl samples
(1% and 10% in reverse Osmosis H$_2$O (MilliQ)).

| Element | 1% NaOCl solution [ppb] | 10% NaOCl solution [ppb] |
|---|---|---|
| Ca | 75.8 | 687 |
| Co | <8 | <80 |

TABLE 3-continued

Result of elemental analyses of two NaOCl samples
(1% and 10% in reverse Osmosis H$_2$O (MilliQ)).

| Element | 1% NaOCl solution [ppb] | 10% NaOCl solution [ppb] |
|---|---|---|
| Cu | <10 | 107 |
| Hg | <0.1 | <1 |
| Fe | <2 | <20 |
| Mg | <0.2 | <2 |
| Mn | <0.6 | <6 |
| Ni | <1 | <10 |

All values are in the acceptable range for high quality NaOCl solutions. As the 1% solution was diluted from the 10% solution the data corresponds well.

Sterilisation

Sterilisation may also affect the available chlorine concentration (Table 4). Possible methods are autoclaving (samples were heated to 121° C. for 15 minutes), γ-sterilisation (samples were γ-irradiated with a dose of 25 to 42 kGy or filtration (samples were filtered over a PVDF 0.2 µm syringe filter).

γ-Sterilisation showed the severest reduction in NaOcl concentration, followed by autoclaving. Filtration over a polyvinylidene fluoride (PVDF) filter did not affect the hypochlorite concentration (see Table 4).

TABLE 4

Effect of sterilisation methods on the concentration of
a 0.7% NaOCl solution. After autoclaving the sample and
γ-sterilisation a reduction of the NaOCl content was
detectable. This was not the case for the filtration.

|  | [NaOCl]$_{initial}$ | [NaOCl]$_{final}$ |
|---|---|---|
| 15 min/121° C. | 0.7% | 0.6% |
| γ-sterilization |  | 0.5% |
| filtration (PVDF) |  | 0.7% |

Shelf Life

Upon storage at 4° C., room temperature and 44° C. in the dark (FIGS. 1-3), 1%, 5% and 10% NaOCl solutions showed similar degradation as predicted by a literature model. High temperature and concentration accelerate the degradation process. In line with these observations are the commercially available NaOCl solutions from Hedinger. Their products are more stable the lower the concentration (1% NaOCl solution: 18 months, 3% NaOCl solution: 12 month). For the 1% NaOCl solution the sample stored at 44° C. showed degradation (FIG. 1). The concentration of the probes stored at 4° C. and room temperature did not change during the time of the experiment. Literature suggests that for a temperature increase of 10° C. degradation is 3.5 times faster. Thus, the sample stored at room temperature corresponds to 10 times the storage time at 4° c.

Storage of a 0.6% NaOCl solution at room temperature exposed to light did not show an immediate effect on the concentration (FIG. 4, square). Storage of the same 0.6% NaOCl solution at 44° C. (pH=11.5) showed degradation after a month (circle). The pH also decreased to 8. Storage of a 0.6% NaOCl solution with excess NaOH (1 M NaOH$_{aq}$ was added until pH>12) did not degrade during the 41 days of the experiment (triangle). Therefore, as soon as the pH drops out of the preferred range (pH=11-13), degradation is dramatically accelerated and that the hypochlorite concentration is affected more by temperature than by natural daily light exposure.

Carbopol Gels

Carbopol is a high molecular weight polymer of acrylic acid, which is commercially available.

Basic solutions 1-4 were prepared for each targeted final NaOCl concentration and directly used in the experiment (Table 5). Each solution has been mixed with 1.0 g carbopol solution.

TABLE 5

|  | amount used | % NaOCl theoretical* | % NaOCl measured | pH |
|---|---|---|---|---|
| final concentration in the hydrogel to be produced: 0.7% NaOCl ||||
| Solution 1 (1M NaOH) | 0.2 g | 4.17 | 4.03 | 14 |
| Solution 2 (0.5M NaOH) | 0.4 g | 2.59 | 2.58 | 13.5 |
| Solution 3 (0.25M NaOH) | 0.8 g | 1.67 | 1.65 | 13.2 |
| Solution 4 (0.1M NaOH) | 2.0 g | 1.03 | 1.01 | 12.5 |
| final concentration in the hydrogel to be produced: 0.3% NaOCl ||||
| Solution 1 (1M NaOH) | 0.2 g | 2 | 2.08 | 14 |

TABLE 5-continued

|  | amount used | % NaOCl theoretical* | % NaOCl measured | pH |
|---|---|---|---|---|
| Solution 2 (0.5M NaOH) | 0.4 g | 1.11 | 1.15 | 23.5 |
| Solution 3 (0.25M NaOH) | 0.8 g | 0.74 | 0.707 | 13.1 |
| Solution 4 (0.1M NaOH) | 2.0 g | 0.48 | 0.505 | ca. 13 |

TABLE 5-continued

|  | amount used | % NaOCl theoretical* | % NaOCl measured | pH |
|---|---|---|---|---|
| final concentration in the hydrogel to be produced: 0.1% NaOCl ||||
| Solution 1 (1M NaOH) | 0.2 g | 0.72 | 0.763 | 13.5 |
| Solution 2 (0.5M NaOH) | 0.4 g | 0.38 | 0.428 | 13.3 |
| Solution 3 (0.25M NaOH) | 0.8 g | 0.26 | 0.265 | 13.1 |
| Solution 4 (0.1M NaOH) | 2.0 g | 0.2 | 0.213 | 12.6 |

The concentration of the solutions should not be too high, as degradation would be accelerated (Table 5, e.g. 4.17% for solution 1 with a final NaOCl concentration of 0.7%). However, a very low hypochlorite concentration is less preferred (e.g. 0.38-0.2% for solution 2-4 with a final NaOCl concentration of 0.1%) due to the fact that only slight changes (e.g. due to trace impurities) during storage may have bigger impact on the concentration in the hydrogel and therefore, on its effectiveness. Nevertheless, the experiment was carried out for all solutions and the desired NaOCl concentration was approximately reached after mixing (Table 6). Hydrogel formation was partially observed, which is indicated by a colour code in Table 6.

TABLE 6

Results of the two-component system. [Carb.]$_i$ stands for the concentration of the used carbopol solution, [NaOCl]$_f$ stands for the target concentration of NaOCl. [NaOCl]$_t$ indicates the titrated final NaOCl concentration (after mixing).

| Sample | [Carb.]$_i$ | [NaOCl]$_t$ Sol. 1 1M NaOH | Sol. 2 0.5M NaOH | Sol. 3 0.25M NaOH | Sol. 4 0.1M NaOH | [NaOCl]$_f$ |
|---|---|---|---|---|---|---|
| Experiment 1 | 1% | 0.70%[1)] | 0.66%[1)] | 0.62%[1)] | 0.65%[1)] | 0.70% |
| Experiment 2 | 2% | 0.55%[3)] | 0.55%[3)] | 0.68%[2)] | 0.81%[1)] |  |
| Experiment 3 | 3% | 0.64%[3)] | 0.63%[3)] | 0.61%[3)] | 0.61%[2)] |  |
| Experiment 1 15 min/121° C. | 1% | 0.62%[1)] | 0.68%[1)] | 0.68%[1)] | 0.64%[1)] |  |
| Experiment 2 15 min/121° C. | 2% | 0.67%[3)] | 0.73%[3)] | 0.65%[2)] | 0.65%[1)] |  |
| Experiment 3 15 min/121° C. | 3% | 0.55%[3)] | 0.64%[3)] | 0.59%[3)] | 0.60%[2)] |  |
| DA050 15 min/121° C. | 1% | 0.33%[2)] | 0.32%[1)] | 0.31%[1)] | 0.33%[1)] | 0.30% |
| DA051 15 min/121° C. | 2% | 0.32%[3)] | 0.27%[3)] | 0.29%[3)] | 0.32%[3)] |  |
| DA052 15 min/121° C. | 3% | 0.26%[3)] | 0.26%[3)] | 0.31%[3)] | 0.30%[3)] |  |
| DA053 15 min/121° C. | 1% | 0.13%[3)] | 0.15%[2)] | 0.12%[1)] | 0.14%[1)] | 0.10% |
| DA054 15 min/121° C. | 2% | 0.09%[3)] | 0.12%[3)] | 0.11%[3)] | 0.14%[3)] |  |

[1)]no gel formation;
[2)]gel-like;
[3)]gel formation.
"15 min/121° C.": autoclaved Carbopol solution 2% Carbopol 974P NF mixed with solution 2 or 3 for a final concentration of 0.1% or 0.3% NaOCl was considered to be a promising range and therefore, the viscosity of these four combinations was measured (FIG. 8) and the yield point was determined (Table 7 and FIG. 9). The higher the NaOCl content and the lower the final Carbopol concentration the lower is the yield point. The viscosity was measured and prepared twice for each sample in order to investigate reproducibility (FIGS. 6 and 7). The yield points and the viscosities show the trend that the more NaOCl is added and the more liquid is added (corresponds to lower base concentration) the less viscous the gel. This was also observed during a different experiment and is displayed in FIG. 8.

TABLE 7

Yield point measurements:

| | Yield point [Pa] |
|---|---|
| 1.2% Carbopol 974P NF | 219 |
| 1.2% Carbopol 974P NF 15 min/121° C. | 143 |
| 1.5% Carbopol 974P NF | 229 |
| 1.5% Carbopol 974P NF 15 min/121° C. | 103 |
| 2% Carbopol 974P NF, 0.1% NaOCl, solution 2 | 80.8 |
| 2% Carbopol 974P NF, 0.1% NaOCl, solution 3 | 47.1 |
| 2% Carbopol 974P NF, 0.3% NaOCl, solution 2 | 43.2 |
| 2% Carbopol 974P NF, 0.3% NaOCl, solution 3 | 19.0 |

Some samples did not form a hydrogel during the two-component experiment. As the amount of the added basic NaOCl solution was dependent on its base concentration and therefore, the Carbopol was diluted to a varied extend. Therefore, the ratio NaOCl/Carbopol may have been too high for some formulations (Table 8).

TABLE 8

Final Carbopol concentrations after mixing with the different amounts of the basic hypochlorite solutions.

| | 1% Carbopol (1 g) | 2% Carbopol (1 g) | 3% Carbopol (1 g) |
|---|---|---|---|
| Solution 1 (0.2 g) | 0.83% | 1.67% | 2.50% |
| Solution 2 (0.4 g) | 0.71% | 1.43% | 2.14% |
| Solution 3 (0.8 g) | 0.56% | 1.11% | 1.67% |
| Solution 4 (2.0 g) | 0.33% | 0.67% | 1.00% |

Carbopol polymers are sensitive to salts in general. In the case of a higher NaOCl concentration, this is a disadvantage, as it has to be compensated by a higher Carbopol concentration in order to induce hydrogel formation. However, to remove the hydrogel from the implant after application this feature may be very useful. Saline, which is used for rinsing, is expected to rapidly liquefy and dissolve the hydrogel and thus simplify its removal.

CONCLUSIONS

Best results could be obtained by two-component system resulting in a hydrogel containing 0.1%-0.3% NaOCl. One syringe contains a suspended Carbopol polymer, preferably Carbopol 974, Carbopol 980 or Carbopol ETD 2020 or a mixture thereof, with a colorant (e.g. methylene blue) at low pH, preferably pH 1 to 3.5, most preferably pH 2 to 3.5, the other contains a NaOCl solution at high pH (e.g. 0.5 M NaOH, 1.11% NaOCl). At low pH, the Carbopol suspension is liquid and the high pH of the NaOCl solution warrants its stability. Prior to application, the two syringes are connected and their contents mixed. Decolouration indicates sufficient mixing and the resulting neutralization of the systems leads to formation of a colourless and transparent hydrogel. The hydrogel contains preferably 0.1%-0.3% NaOCl (depending on storage time) and it has a pH of 6.5-7.5.

The invention claimed is:

1. A two-component system for the preparation of a hydrogel having a viscosity of more than 40,000 mPa*s at 20° C. for preventing and/or treating a periodontal disease, comprising:
   a) as a first component, an aqueous suspension having a pH value of less than 7 comprising at least one pH-sensitive gelling agent,
   b) as a second component, a sodium hypochlorite (NaOCl) solution at a pH in the range of 10 to 13, a concentration of the sodium hypochlorite solution in the second component being in a range of from 0.7 to 4.2% by weight,
   wherein the first component is physically separated from the second component.

2. The two-component system according to claim 1, wherein the suspension comprising the at least one pH-sensitive gelling agent has a viscosity of less than 4000 mPa*s at 20° C.

3. The two-component system according to claim 1, wherein the sodium hypochlorite solution of the second component has a pH in a range of from 11 to 13.

4. The two-component system according to claim 1, wherein the at least one pH-sensitive gelling agent is a crosslinked polyacrylic acid.

5. The two-component system according to claim 1, wherein the aqueous suspension comprising the at least one pH-sensitive gelling agent additionally comprises a non-toxic pH sensitive colorant.

6. The two-component system according to claim 1, wherein said system is a dual cartridge or a dual syringe.

7. A hydrogel obtainable by mixing the two components of the two-component system according to claim 1.

8. The hydrogel according to claim 7, wherein the hydrogel has a pH in a range of from 6.0 to 9.5.

9. The hydrogel according to claim 6, wherein the hydrogel has a sodium hypochlorite concentration in a range of from 0.1 to 0.7% by weight of the total weight of the gel.

10. A kit of parts for treating a periodontal disease, selected from the group consisting of periimplantitis, gingivitis, periodontitis, and peri-implant mucositis, comprising:
   (a) the two-component system according to claim 1, and
   (b) a composition comprising chlorhexidine (CHX).

11. The kit of parts according to claim 10, wherein the composition comprising chlorhexidine is an aqueous solution or a hydrogel.

12. The kit of parts according to claim 10, wherein the composition comprising chlorhexidine is a two-component system comprising:
   (a) as a first component, an aqueous suspension comprising a pH-sensitive gelling agent, and
   (b) as a second component, a chlorhexidine solution having a pH which is above the gelling pH of the at least one pH-sensitive gelling agent.

13. A method for treating a periodontal disease selected from the group consisting of periimplantitis, gingivitis, periodontitis, and peri-implant mucositis, the method comprising:
   administering the hydrogel according to claim 7 to a site of infection in a patient suffering from the periodontal disease.

14. The two-component system according to claim 2, wherein the viscosity of the suspension comprising the at least one pH-sensitive gelling agent is less than 1500 mPa*s at 20° C.

15. The two-component system according to claim 3, wherein the pH of the sodium hypochlorite solution of the second component is in a range of from 11 to 12.

16. The two-component system according to claim 5, wherein the non-toxic pH sensitive colorant is selected from the group consisting of methylene blue, indigocarmine, methyl green, bromocresol green, sodium alizarine sulphonate, chlorophenol red, bromthymol purple, bromthymol blue, azolitmin, neutral red, cyanine, phenol, phenol red, cresol red, thymol blue, α-Na phenolphthaleine, phenolphthaleine, α-Na phthalein, thymolphthaleine, nile blue, alizarine yellow, methyl violet, methyl yellow, bromphenol blue, paranitrophenol, bromphenol purple, and litmus.

17. The two-component system according to claim 16, wherein the non-toxic pH sensitive colorant is methylene blue or litmus.

\* \* \* \* \*